United States Patent
Jesenko et al.

(10) Patent No.: US 10,456,225 B2
(45) Date of Patent: Oct. 29, 2019

(54) METHOD FOR CLEARING OF VIRTUAL REPRESENTATIONS OF OBJECTS

(71) Applicant: a.tron3d GmbH, Klagenfurt am Woerthersee (AT)

(72) Inventors: Juergen Jesenko, Riegersdorf (AT); Engelbert Kelz, Klagenfurt (AT)

(73) Assignee: A. TRON3D GMBH, Klagenfurt am Woerthersee (AT)

( * ) Notice: Subject to any disclaimer, the term of this patent is extended or adjusted under 35 U.S.C. 154(b) by 190 days.

(21) Appl. No.: 15/783,251

(22) Filed: Oct. 13, 2017

(65) Prior Publication Data

US 2018/0104029 A1   Apr. 19, 2018

(30) Foreign Application Priority Data

Oct. 13, 2016  (EP) .................................. 16193819

(51) Int. Cl.
*A61B 5/055* (2006.01)
*A61C 19/04* (2006.01)
(Continued)

(52) U.S. Cl.
CPC ........ *A61C 13/0004* (2013.01); *A61B 5/0088* (2013.01); *A61B 5/055* (2013.01);
(Continued)

(58) Field of Classification Search
CPC ....... A61B 5/0088; A61B 5/055; A61C 9/004; A61C 9/0053; A61C 13/0004;
(Continued)

(56) References Cited

U.S. PATENT DOCUMENTS

| 8,538,105 B2 * | 9/2013 | Masumoto ............ G06T 7/0012 378/4 |
| 9,017,071 B2 * | 4/2015 | Hultgren .................. A61C 7/00 433/24 |

(Continued)

FOREIGN PATENT DOCUMENTS

WO   2013010910 A1   1/2013

OTHER PUBLICATIONS

Perera et al. ("Motion segmentation of truncated signed distance function based volumetric surfaces," IEEE Winter Conference on Applications of Computer Vision, Jan. 5-9, 2015) (Year: 2015).*

(Continued)

*Primary Examiner* — Yubin Hung
(74) *Attorney, Agent, or Firm* — Young & Thompson (57) ABSTRACT

A method for clearing unwanted data from optically detected virtual representations of objects includes: a. Defining an extension line of the representation; b. Generating a projection plane at one point of the extension line, which is perpendicular to the generated projection plane; c. Projecting all known points in space of the representation from one region on the projection plane onto the projection plane, the corresponding point in space being stored for each projected point; d. Generating a two-dimensional curve on the projection plane; e. Determining maxima, minima and a center of the curve; f. Identifying projected points of the curve that—viewed from the center of the curve—lie outside of the minima or maxima; g. Removing the points in space that correspond to the projected points that were identified in step f.; and h. Optionally, repeating starting from step b. for one further point of the extension line.

20 Claims, 6 Drawing Sheets

(51) Int. Cl.

| | | |
|---|---|---|
| *G06T 19/20* | (2011.01) | |
| *A61C 13/00* | (2006.01) | |
| *H04N 13/167* | (2018.01) | |
| *A61B 5/00* | (2006.01) | |
| *A61C 9/00* | (2006.01) | |
| *G06K 9/34* | (2006.01) | |
| *G06T 7/11* | (2017.01) | |
| *G06F 17/50* | (2006.01) | |
| *H04N 5/74* | (2006.01) | |

(52) U.S. Cl.
CPC .............. *A61C 9/004* (2013.01); *A61C 19/04* (2013.01); *G06K 9/34* (2013.01); *G06T 7/11* (2017.01); *G06T 19/20* (2013.01); *H04N 13/167* (2018.05); *A61C 9/0053* (2013.01); *G06F 17/50* (2013.01); *G06T 2200/04* (2013.01); *G06T 2207/10028* (2013.01); *G06T 2207/30036* (2013.01); *G06T 2219/2021* (2013.01); *H04N 5/7416* (2013.01)

(58) Field of Classification Search
CPC .......... A61C 19/04; G06F 17/50; G06K 9/34; G06T 7/11; G06T 19/20; G06T 2219/2021; G06T 2200/04; G06T 2207/10028; G06T 2207/30036; H04N 5/7416; H04N 13/167
See application file for complete search history.

(56) References Cited

U.S. PATENT DOCUMENTS

| | | | |
|---|---|---|---|
| 2002/0037489 A1 | 3/2002 | Jones et al. | |
| 2005/0117787 A1* | 6/2005 | Iordanescu | G06T 7/60 382/128 |
| 2007/0072144 A1* | 3/2007 | Imgrund | A61C 7/00 433/24 |
| 2008/0281543 A1* | 11/2008 | Jia | G01B 11/25 702/97 |
| 2009/0079738 A1* | 3/2009 | Liao | G06T 19/00 345/427 |
| 2009/0184865 A1* | 7/2009 | Valo | G01S 7/412 342/25 F |
| 2011/0115791 A1* | 5/2011 | Sabiston | A61F 2/5046 345/419 |
| 2011/0184695 A1* | 7/2011 | Grzesiak | G01B 5/008 702/167 |
| 2013/0022255 A1* | 1/2013 | Chen | G06K 9/34 382/131 |
| 2015/0024337 A1 | 1/2015 | Blassnig et al. | |
| 2016/0070821 A1 | 3/2016 | Somasundaram et al. | |
| 2016/0081645 A1* | 3/2016 | Fukuda | A61B 6/5205 378/4 |
| 2017/0056451 A1* | 3/2017 | Meron | A61K 35/37 |
| 2017/0340268 A1* | 11/2017 | Danielsson | A61B 5/4561 |

OTHER PUBLICATIONS

Pavaloiu et al. ("Automatic segmentation for 3D dental reconstruction," 6th International Conference on Computing, Communication and Networking Technologies (ICCCNT), Jul. 13-15, 2015) (Year: 2015).*

Yu-Bing Chang, et al., An Automatic and Robust Algorithm of Reestablishment of Digital Dental Occlusion, IEEE Transactions on Medical Imaging, Sep. 2010, pp. 1652-1663, vol. 29, No. 9.

Hui Gao, et al., Automatic Tooth Region Separation for Dental CT Images, Third 2008 International Conference on Convergence and Hybrid Information Technology, 2008, pp. 897-901.

Toshiaki Kondo, et al., Tooth Segmentation of Dental Study Models Using Range Images, IEEE Transactions on Medical Imaging, Mar. 2004, pp. 350-362, vol. 23, No. 3.

Mingxi Zhao, et al., Interactive Tooth Segmentation of Dental Models, Proceedings of the 2005 IEEE: Engineering in Medicine and Biology 27th Annual Conference, Sep. 2005, pp. 654-657.

Nov. 27, 2017, EP communication issued for related EP application No. 17196228.5.

Mar. 20, 2017, EP communication issued for related EP application No. 16193819.

* cited by examiner

METHOD FOR CLEARING OF VIRTUAL REPRESENTATIONS OF OBJECTS

The invention relates to a method for clearing, in particular for removing, unwanted data from optically detected virtual representations of objects, in particular teeth and intraoral structures.

Many systems for the optical detection of the three-dimensional geometry of objects are known in particular in the area of dental treatments. They are used in, for example, the production of prostheses, crowns, inlays or the like, serve for support in the monitoring of orthodontic treatments and/or help in the observation or detection of intraoral structures in general. On the one hand the major advantage of these optical systems is that they are neither invasive nor unpleasant, such as, for example, the dental impression that is often used in conventional dentistry, nor do they constitute a potential risk to patients, as can be the case, for example, in radiation-based methods, such as the x-ray. On the other hand, the data are in electronic form after acquisition and can be easily stored, for example for later comparisons, or else transmitted, for example from a dentist to a dental laboratory.

One problem that arises constantly in optical methods for detection of the three-dimensional geometry of objects, in particular teeth, is that soft parts that are present in the oral cavity, such as the inside of the cheeks or the tongue, are unintentionally acquired. Later correction of these faulty recordings is usually difficult since even in systems that provide several pictures of the same region, the faulty pictures are included in the detected or computed geometry too and corrupt it. Furthermore, unintentionally photographed surfaces constitute an unnecessary additional data volume that under certain circumstances can slow various processes, such as, for example, the visualization of the detected surface geometry.

The approaches to this problem that have been undertaken so far in the state of the art follow mainly two basic strategies. In one strategy, the surfaces that have been defectively acquired are identified as such and removed. One example of this first approach is shown by WO 2013/010910 A1. In the second strategy, empty spaces are defined or identified in which there can be no surfaces, and surfaces that are consequently measured as located in these empty spaces are either removed by the system when identification takes place after measurement, or are ignored from the start. One example of this approach is shown in EP 2 775 256 A1.

It is common to the two systems that during or after scanning, either incorrectly detected surfaces or empty spaces must be actively acquired or recognized as faults; this, on the one hand, requires computer resources and, on the other hand, is susceptible to errors.

Therefore, the object of the invention is to overcome the above-described disadvantages and to make available a simplified method for clearing unwanted surface regions. Preferably, it should also be possible for it to be executed independently of a surface that has been detected at the instant of clearing. This means even without the fault being able to be referenced to an at least partially "finished" surface.

This object is achieved according to the invention by a method of the initially described type, which is characterized in that the method includes the following steps:

a. Defining of an extension line of the representation,
b. Generating of a projection plane at one point of the extension line, the extension line being perpendicular to the generated projection plane, in that point,
c. Projecting of all known points in space of the representation from a region by the projection plane onto the projection plane, whereby for each projected point, at least one corresponding point in space is stored,
d. Generating a two-dimensional curve on the projection plane from the projected points,
e. Determining of maxima, minima and a center of the curve,
f. Identifying of projected points of the curve that viewed from the center of the curve lie outside of the minima or maxima,
g. Removing of the points in space, which correspond to the points identified in step f,
h. Optionally, repeating starting from step b. a further point of the extension line.

The extension line which is defined in step a) essentially follows the mandibular arch in this case. Possible ways to generate various exact extension lines are explained in later sections.

The plane that has been generated perpendicular to the extension line at a point of the extension line in step b) can also be regarded as a section through the representation.

The projecting from step c) consequently shows essentially the profile of the representation in the section or in the plane of step b). The region can be variously selected in doing so, as is further explained below.

In step d), a two-dimensional curve is generated from the projected points of step c). It can contain various sub-steps, for example for smoothing the curve or for closing gaps. Some possible intermediate steps from step d) are likewise further explained below.

In step e), the maxima and minima as well as a center of the curve are determined. Depending on whether the object in the region of the plane or of the section is a buccal tooth or an incisor, and whether it is located in the upper or lower jaw, the center will be roughly in the area of one or two largest maxima or minima of the curve. This center then lies essentially in the center of the tooth, and the minima or maxima lie on the tips of the teeth. The minima or maxima that are farther away from the center consequently correspond ordinarily to a transition between the gums and other soft tissue, such as, for example, the tongue or the inside of the cheek. If a center cannot be defined in this way, the arithmetic mean between the two end points of the curve can be defined as the center instead.

If, as provided in step f), all points are identified that lie outside of the outer maxima or minima viewed from the center, the unwanted regions are also automatically identified without active recognition of these structures being necessary for this purpose. Of course, the border for identification can also be stipulated to be somewhat outside of the maxima or minima in order not to unintentionally remove desired data.

In step g), all corresponding points in space that correspond to the projected and identified points can then be removed. Consequently, a cleared representation is obtained without the need to actively determine incorrect or correct surfaces in a complicated method for this purpose.

This can then take place in steps for any number of points of the extension line as is defined in step h). The individual planes or sections along the extension line are preferably spaced in this case such that each part of the representation lies in at least one (of the) region(s) from step c) and has been projected onto one of the planes from step b).

In order to computationally simplify the dividing, the planes or sections can preferably be generated equidistantly on the extension line.

Other preferred embodiments of the invention are the subject matter of the remaining dependent claims.

Preferred exemplary embodiments of the invention are described in more detail below using the drawings. Here.

Figure 1:
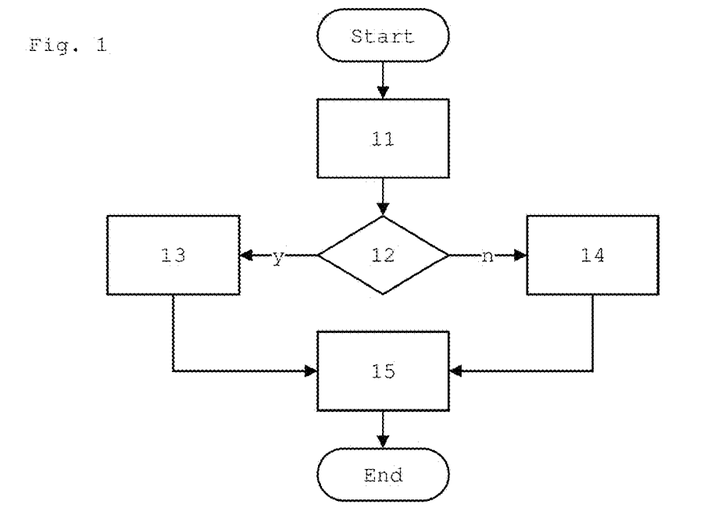
FIG. 1 shows a method for computational simplification of a three-dimensional representation, in particular of a truncated signed distance function (TSDF)

FIG. 1 shows a method for computational simplification of a three-dimensional representation, in particular of a TSDF. Here, a model to be cleared is first subdivided into coarser sections. For this purpose, groups of voxels are each combined into so-called bricks. A brick in this case is preferably a cube of $n^3$ voxels, preferably $8^3$ voxels. The representation is subdivided in step 11.

Then, for each brick, the information as to whether the voxels of the brick contain surface information is retrieved (step 12).

If it is ascertained that at least one voxel of the brick contains a surface, a center point of the brick is notated as a location vector. Here, the location vector corresponds to a connection of an origin of a coordinate system, in which the TSDF is notated, to the center point of the brick (step 13).

If a brick does not contain any voxels that contain surface information, it is marked, for example, as "empty" (step 14).

Then, all empty bricks and location vectors are combined into a common point cloud. However, for each location vector it is stored, to which voxels it corresponds (step 15).

Figure 2:
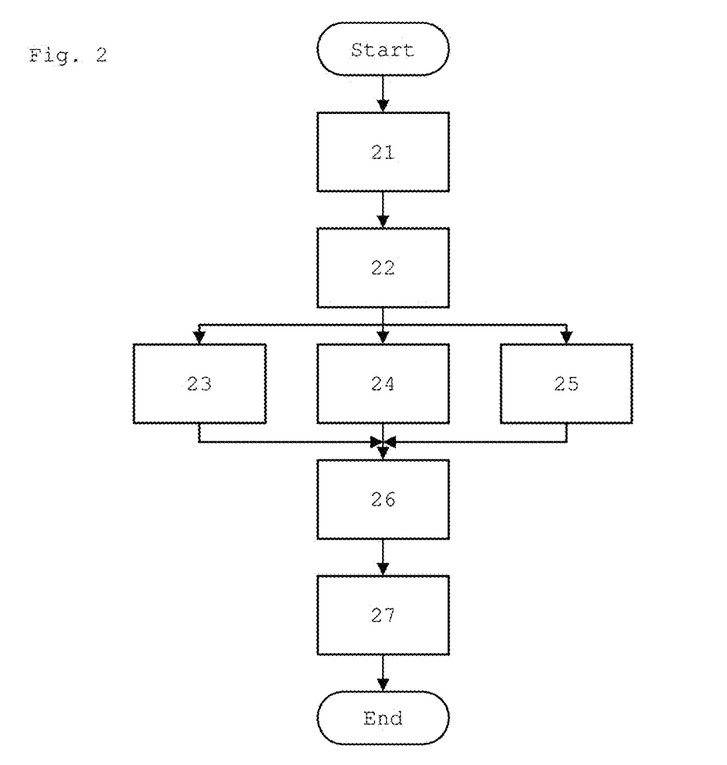
FIG. 2 shows a method for determining principal axes.

FIG. 2 shows a first possible method for determining the principal axes. To do this, first of all, in a step 21, the covariance matrix of a point cloud is determined. This can be, for example, the simplified point cloud from the above-described steps 11 to 15. It is also possible, however, to work directly with a representation that is present in the form of a point cloud. In the subsequent step 22, the three eigenvectors of the covariance matrix from step 21 are determined. For three-dimensional point clouds, the covariance matrix will always deliver three eigenvectors. If the eigenvectors are determined, they are defined as the axial directions of a coordinate system. In a 3×3 covariance matrix, as it results from a three-dimensional point cloud, the axial directions are always orthogonal to one another, as in a Cartesian coordinate system. For the z-axis, the direction of the smallest eigenvector is selected (step 23). For the y-axis, the direction of the largest eigenvector is selected (step 24). For the x-axis, accordingly the middle eigenvector is selected (step 25). As is apparent to one skilled in the art, steps 23 to 25 can be executed in any sequence, or even in parallel, as shown. Furthermore, in a step 26, the center of gravity of the point cloud is determined. It is then established in a step 27 as the origin of the coordinate system. Of course, the center of gravity can be determined independently of the other steps of the method shown in FIG. 2 (aside from step 27). With sufficient computing power, this step can proceed, for example, also in parallel to the other steps. The coordinate system that has been generated in this way with its principal axes with respect to the point cloud can be advantageously used in later steps of the method.

Figure 3:
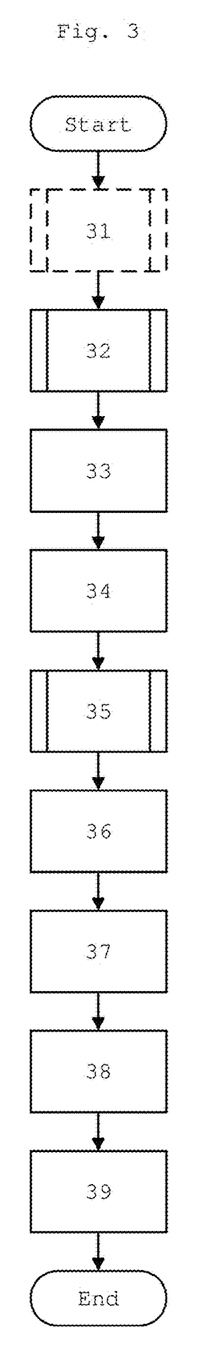
FIG. 3 shows by way of example a method according to the invention.

FIG. 3 shows an exemplary method according to the invention. For this purpose, in step 31, a virtual representation can be simplified first, as described for FIG. 1. This is not critically necessary for the invention, however. For example, in certain formats in which the representation can be present, this step can also be omitted. Steps that are self-evident, such as, for example, providing or loading the representation or such as the subsequent storing, are not individually cited or depicted for the sake of the clarity of the illustrated method. Corresponding steps before and after the actual method according to the invention can be chosen accordingly by one skilled in the art. The same also applies, of course, to the sequence of selected steps.

In the next step 32, an extension line for the representation is chosen. A highly simplified extension line is a straight line along the representation. One example of such a straight line can be the y-axis of the principal axes determined in FIG. 2, or the longest of the stipulated axes. Curved extension lines, however, can also be determined.

Figure 11:
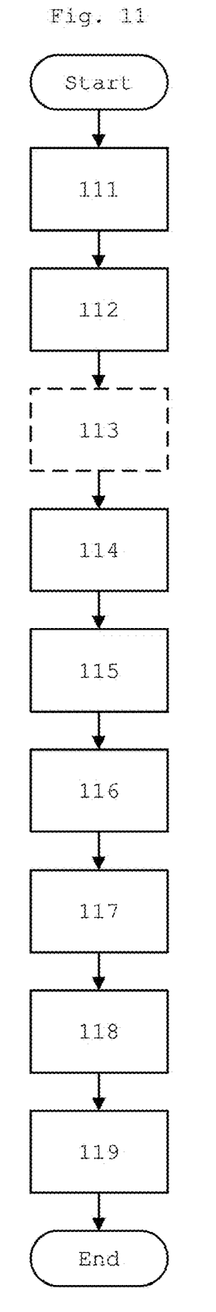
FIG. 11 shows an alternative method for arriving at an extension line.
Figure 12:
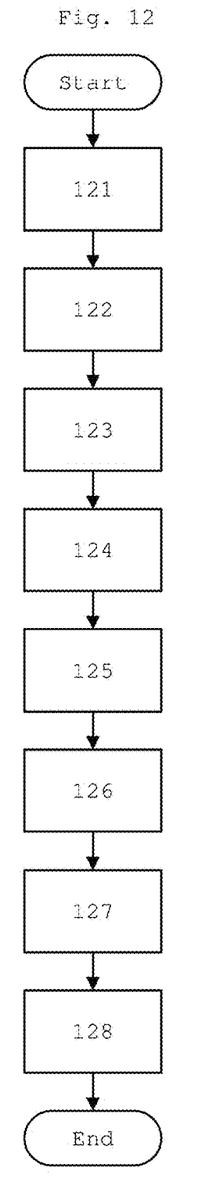
FIG. 12 shows an alternative method for determining principal axes.
Figure 13:
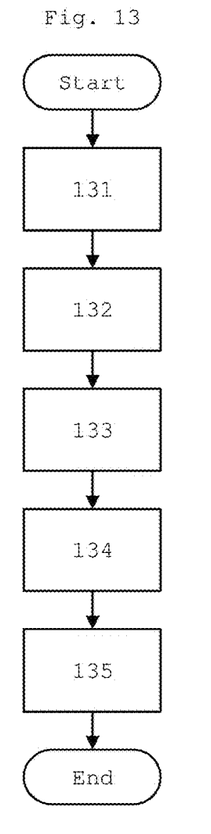
FIG. 13 shows another alternative method for generating an extension line.
Figure 14:
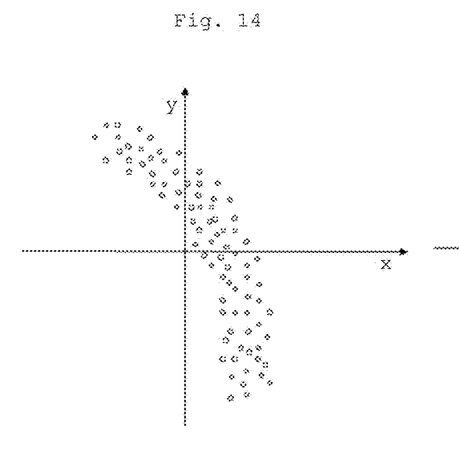
FIG. 14 shows a highly simplified representation of steps 111 to 114 from FIG. 11.

Examples for possible determination of curved extension lines are found in FIGS. 11 and 13 as well as in the explanatory FIGS. 14 to 17 for FIG. 11. One alternative method for determination of principal axes whose y-axis can be used as the extension line is shown in FIG. 12.

In a next step 33, planes of intersection of the (optionally simplified) representation are generated. They are each aligned perpendicular to the extension line. If the extension line is a straight line, the planes of intersection are consequently parallel. Preferably, the planes of intersection along the extension line are equidistantly generated. If the representation in step 31 has been simplified, "slices" in the thickness of one or two bricks at a time (for example, 8 or 16 voxels thick) are suitable. A stipulation of the distances of the slices can also be based upon the actual sizes of the represented object regardless of the voxel subdivision. Thus, for example, a distance of 2 mm can be selected. Here, one "slice" corresponds to the region in front of and/or behind the plane of intersection, preferably to the region in front of each plane of intersection viewed in the direction of the extension line. However, for example, several "slices" can also together form the region. In doing so, "slices" in front of and behind the plane (viewed along the extension line) can also be chosen. For curved extension lines, consequently "wedges" form that can build the regions around the extension lines.

In a following step 34, the points in the regions are projected onto the plane. In very simple applications of the invention, for example, all points within the region (which are therefore located in the "slice") can be mapped along perpendiculars onto the plane. Alternatively, a projection can also take place along perpendiculars of an adjacent plane.

Figure 4:
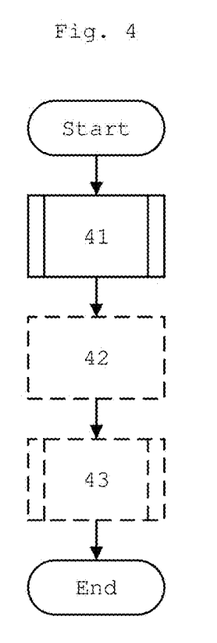
FIG. 4 shows a method for determining a curve.

In step 35, a two-dimensional curve on the plane is determined. To do this, for example, all imaged points can simply be joined. One preferred and advantageous method with different optional variants for generating a two-dimensional curve is shown by FIG. 4, which is further described below.

With the curve that has been generated in this way (see, for example, 71, 72 in FIG. 7), steps 36 and 37 can then be executed according to the invention. To do so, one center (for example, 73 in FIG. 7) and minima and maxima (for example, 74 and 75 in FIG. 7) to the left and right of the center are determined. It is advantageous but not essential if the center of the curve is determined first.

In order to be able to actually indicate criteria for distinguishing between teeth and artefacts, such as, for example, parts of a cheek, in this process, as provided according to the invention, the orientation of the coordinate system to the (optionally simplified) model must be considered, depending on whether a "hanging" tooth or a "standing" tooth is being examined; either "maxima" or "minima" are selected as criteria.

In general, all considerations, inasmuch as they relate to minima or maxima, can accordingly also be used reversed. For the sake of clarity, described below is only the procedure for a model in which the teeth and surrounding intraoral structures are oriented such that the tips of the teeth point down. All considerations can be easily transferred by one skilled in the art to models with tips of the teeth that point up.

Figure 7:
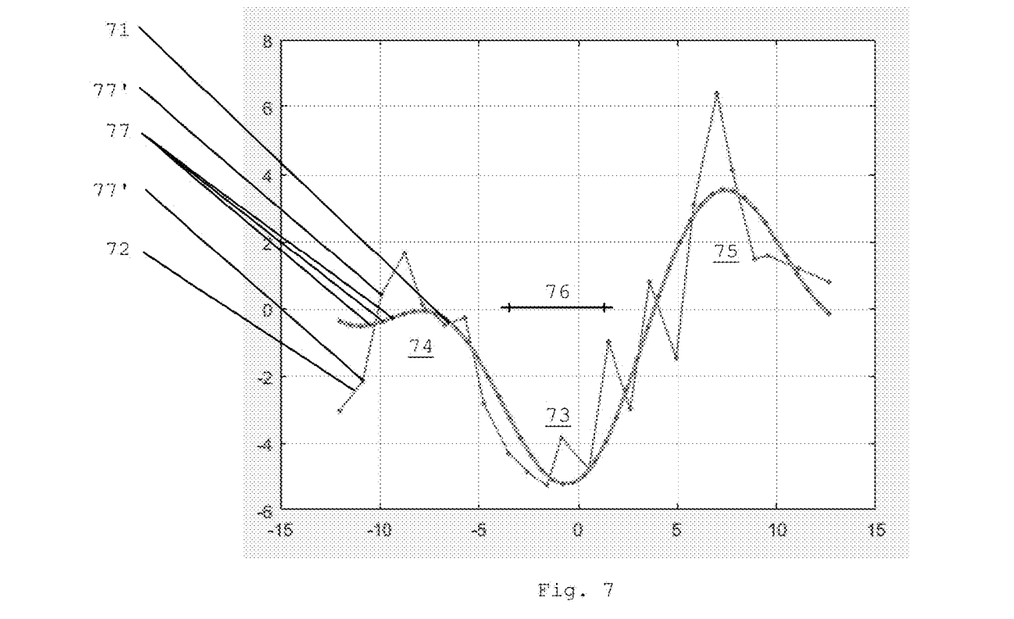
FIG. 7 shows examples of curves.

If the teeth, as in the illustrated example from FIG. 7, lie with the crowns pointing downward, it holds true that the curves of the intersection of a tooth that has been captured free of faults and unwanted surfaces and artefacts must run essentially in a U-shape. If molars have been captured, W-shaped plots are possible, since the teeth in this region have more than one tip. It is therefore examined whether there are relative maxima that are to the left or right of the center of the curve of the intersection. Maxima that lie near the center of the curve are not considered since the crown of the tooth can also contain maxima due to fissures. Therefore, preferably a region near the center (see 76 in FIG. 7) remains ignored when the relevant maxima or minima are being determined.

In the then following step 38, the points of the curve that lie outside of the established maxima (or minima) (see 77 and 77' in FIG. 7) are marked. In order to avoid an unwanted corruption of the representation in this case, a "safety clearance" to the maxima (see 74, 75 in FIG. 7) can be set in the curve.

In step 39, the points in space or data in the voxels of the TSDF that correspond to the points of the curve that were marked in the preceding step are then erased or set to "unknown" and thus are removed from the representation. With this, the clearing is completed. The process of marking voxels as "unknown" or "unseen" is described in more detail in, for example, US 2015/0024337 A1.

Figure 5:
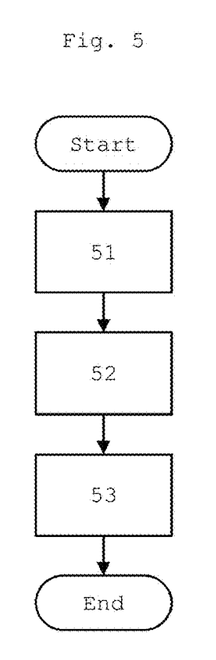
FIG. 5 shows a method for determining the points of the curve.
Figure 6:
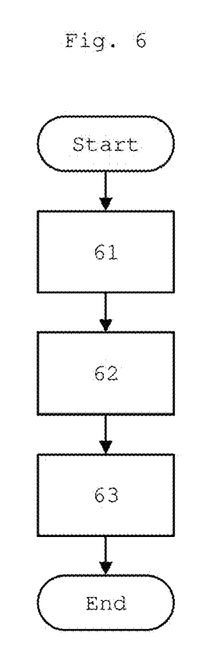
FIG. 6 shows a method for smoothing the curve.

FIG. 4 shows one possible embodiment for point 35 from FIG. 3. In step 41, first the projected points are determined. For this purpose, simply the points that have been projected can be used. A further embodiment of the invention in which the points are determined with a further developed preferred method is shown by FIG. 5. In step 42, optionally additional points can be added to the points. This can take place by linear interpolation between two adjacent points at a time. The higher density of points can be advantageous for various other methods. Likewise, optionally the curve can then be smoothed in step 43. One possible method for the smoothing of the curve is shown by FIG. 6.

In the preferred method for generating points of the curve that is shown in FIG. 5, the points that have been projected and that are now in a two-dimensional point cloud are subdivided into preferably vertical segments or strips of uniform width. If the model has been simplified beforehand in step 31 (or steps 11 to 15), strips in the width from one to two bricks are suitable. Then, in a step 52, for each segment a (two-dimensional) center of gravity is determined. The centers of gravity that have been determined in step 52 are then notated as points of the curve. Thus, even inaccurate point clouds in which there are several (possibly contradicting one another) surface data can be simplified into data that can be easily further processed.

The points that are obtained in step 52 are then entered in step 35 on the plane from step 33 as points of the curve.

In doing so, it can happen that the curve is very "serrated"; this can be disadvantageous for different analyses. That is why the curve, as already mentioned, can be smoothed in step 43. FIG. 6 shows one option for doing this. First, in a step 61, a Fourier transform is applied to the curve from steps 41 and 42. In the next step 62, all frequencies except the base frequency and the first harmonic are removed. Optionally, the second harmonic can also be retained. If the Fourier transform is then carried out backwards in step 63, a visibly smoothed curve (compare 71 and 72 in FIG. 7) is obtained on which minima and maxima can be easily ascertained (73, 74 and 75 in FIG. 7).

FIG. 7 shows an example for each a smoothed curve 71 and an unsmoothed curve 72 with points 77 and 77' respectively. In both curves, a middle region 76 with one minimum 73 and the two maxima 74 and 75 can be recognized.

In one preferred alternative further embodiment of the invention, a common distance for all centers can also be set after determining the center of the curve. It can correspond in particular to half of the entire thickness of a molar, in particular ⅔ of the thickness of a molar. For this purpose, for example, a measured thickness can be added. In case there is still too little data for such statements about the object to be measured, for example, statistical data can, however, also be used to choose a corresponding distance. Conventionally, however, a distance of from 5 mm to 7 mm will be suitable.

In order, however, to avoid distortion of the representation in this method, it is useful to optimize the centers before applying the distance to the centers with respect to the probability that the centers lie on the actual tooth centers. For this purpose, the centers that were determined beforehand in the curves on the planes or sections are projected onto a center projection plane that has been spanned between the x- and the y-axis. Then a center curve is formed on the center projection plane at these points. Methods of forming these curves and additionally optimizing them in amelioration are explained for FIGS. 11 and 17.

If the center curve has been formed, the components of the representation that are outside of the distance that is to be stipulated can be removed. For this purpose, it is not necessary to use these new centers in the sections or planes. The distance can be much more easily applied directly in the entire model (regardless of the sections). To do this, two parallel curves to the center curve are simply produced at a predetermined or stipulated distance. These parallel curves are then spanned perpendicularly to the center projection plane (therefore along the z-axis) to (parallel) surfaces. The region between the surfaces is then left in the representation. The region outside is removed.

The resulting boundary surfaces can be applied in another further development of the method that is independently of the invention advantageous in order to avoid future faulty data when the representation is being acquired. To do this, the regions outside of the parallel surfaces are blocked from the start and spatial information that is being acquired within these regions is simply not considered, for example when the representation is being generated.

Figure 8:
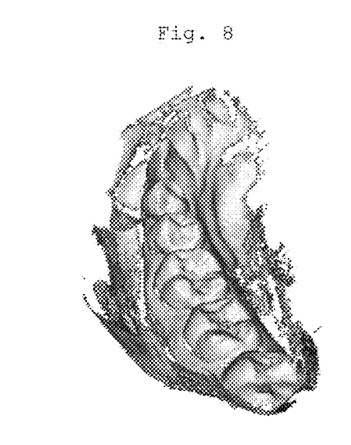
FIG. 8 shows by way of example the visualization of an optically detected jaw section.
Figures 9, 10:
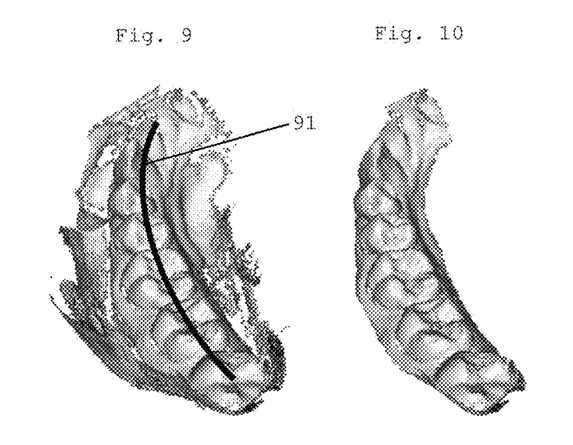
FIG. 9 shows the exemplary visualization from FIG. 8 with an extension line.
FIG. 10 shows an exemplary visualization of a cleared representation that corresponds to FIGS. 8 and 9.

FIGS. 8, 9 and 10 each show, by way of example, a visualization of the representation before clearing (FIG. 8), with a symbolically entered curved extension line 91 (FIG. 9), and after clearing (FIG. 10).

FIG. 11 shows a first method with which a curved extension line can be determined. In doing so, first a coordinate system is loaded in step 111. Methods for producing it are shown, for example, in FIGS. 2 and 12. In the following step 112, an extension projection plane is produced that is spanned between the x- and y-axis of the coordinate system. Optionally, at this point in step 113, an extension projection region can be defined. The simplest option here is to project the complete model. In this case, the entire model is determined as a projection region. A second option is to project only half of the model, preferably that half in which the crowns of the teeth are located. The advantage here is that the shape of the mandibular arch emerges more distinctly in this way. In this case, for example, the half above or underneath the extension projection plane can be defined as a projection region. Another option is a slice-shaped projection region, the boundaries of the slice being parallel to the extension projection plane and preferably having only a short distance to one another. Here, too, the advantage is that the shape of the dental arch can be especially easily recognized.

Figure 15:
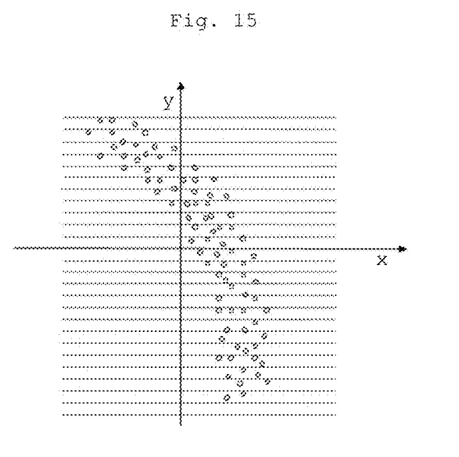
FIG. 15 shows a highly simplified representation of step 115 in FIG. 11.

After the projection region has been defined, in step 114, all points of the projection region are projected vertically (therefore following the z-axis of the coordinate system) onto the extension projection plane. This yields a 2D point cloud (shown symbolically and highly schematically in FIG. 14). In step 115, this point cloud is then subdivided into equally large strips that each run parallel to the x-axis (FIG. 15).

Figure 16:
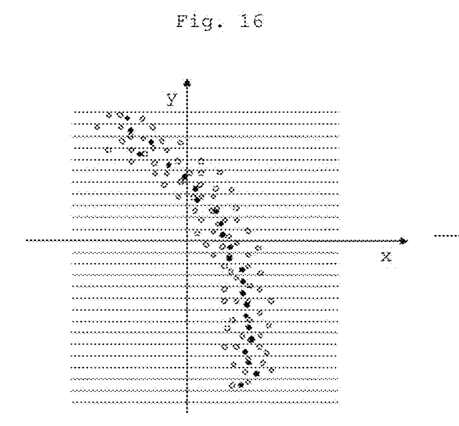
FIG. 16 shows a highly simplified representation of steps 116 to 118 in FIG. 11.

Within each strip, in step 116, the largest and the smallest x-values are then determined, and in step 117, the arithmetic mean is formed. From the arithmetic mean from step 117 and the center of the strip on the y-axis, in step 118, a point that is assigned to one strip at a time and that is shown black in FIG. 16 is then determined for each strip. If, for example, as a result of gaps in the measurement and/or the projection, a strip does not contain any points, this strip is ignored in the following steps.

Then, in step 119, a curve can be determined from the points from step 118. One especially suitable and preferred method for this purpose is the method of least squares. Other approximation methods can also be used, however. One possible approximated curve 172 that originated according to the method shown in FIG. 11 is shown by FIG. 17.

Figure 17:
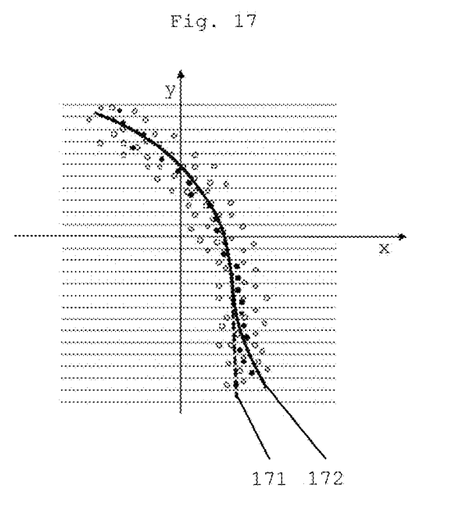
FIG. 17 shows a highly simplified representation of step 119 in FIG. 11 with one additional optional expansion of the method from FIG. 11.

Furthermore, FIG. 17 illustrates an optional amelioration of the method from FIG. 11.

Figure 18:
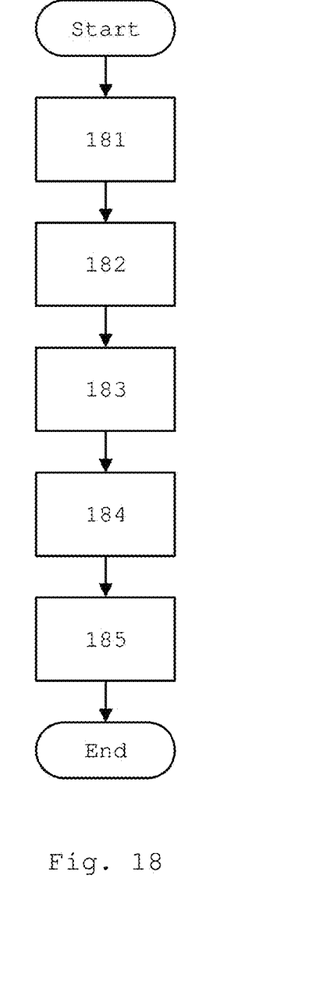
FIG. 18 shows another alternative method for generating an extension line.

It has been shown that an approximation to a third-degree polynomial fits especially well to the shape of a dental arch in the anterior region (incisors) of said arch. However, in the posterior region (thus in the direction of the molars) the curve deviates farther from the shape of the mandibular arch than a simple straight extension line. In order to maintain the advantages of the good approximation of the polynomial in the anterior region and to still avoid the major deviation in the posterior region, in an advanced embodiment of the method from FIG. 11, a combined extension line is formed. To do this, first a third-degree polynomial is produced in the manner illustrated in FIG. 11. Then, the inflection point and the inflection tangent of the polynomial are determined. Then, in the anterior region, the polynomial is stipulated as the extension line, and starting at the inflection point the inflection tangent is stipulated as the extension line. One such alternative course of the extension line is illustrated by the broken line 171 in FIG. 17. Of course, this advanced embodiment can also be applied to other methods for determining a curved extension line in which a third-degree polynomial is determined in order to approximate the shape of the dental arch. These fundamental explanations also apply to the method that is shown in FIG. 18.

FIG. 12 shows one alternative method for producing principal axes that can take place in step 32. To do so, first the normal vectors of the surface of the representation are determined in a step 121. For this purpose, if the representation is in this notation, the TSDF can be used. If the notation as shown in FIG. 1 has been simplified, the normal vector for each voxel of the brick containing one surface is determined, and then an average normal vector is generated by all normal vectors being vector-added and the resulting vector then being brought again to length 1. The resulting vector is then defined as the normal vector of the brick.

In the subsequent step 122, the normal vectors from step 121 are projected onto a unit sphere (Gaussian projection). The origin of the coordinate system in which the representation or its simplification is notated can be simply used as the center point of the unit sphere. Alternatively, the center of gravity of the representation can be used. Both variants are covered, for example, at the same time when the coordinate system in which the representation or its simplification is notated has been produced according to the method that is shown in FIG. 2.

The Gaussian image that has been formed in step 122 can then be examined for free surfaces in the following step 123. In doing so, it is assumed that even if the model has gaps in which no data could have been acquired, in any case no data can be acquired in the region of the jawbone itself. Therefore to identify a larger region in which nothing has been imaged on the sphere at the same time means to identify the jaw or the "origin" of the represented tooth. If then in step 124, a center of this region is determined and then in step 125 a connection is drawn from the center point of the sphere to the center point of the region, it can be assumed that this connection corresponds essentially to the alignment of the represented teeth. Consequently, the connection that was generated in step 125 is stipulated as the direction of the z-axis. In this way, an optimum alignment of the representation to the coordinate system is effected.

One method for determining the (approximate) center of the empty region in step 124 could, for example, consist in that first the center of gravity of all imaged points on the Gaussian sphere is determined. This center of gravity of the imaged points on the Gaussian sphere is then offset somewhat from the center point and will be exactly opposite the empty region. If then a connection is drawn from the center of gravity of the imaged points on the Gaussian sphere to the center point, it points automatically in the direction of the center of the empty region. It must then only still be set to length 1 (while retaining the direction), and the above-described vector that is then stipulated as the z-axis in step 125 is obtained.

In step 126, first the largest eigenvector of the representation is determined for the determination of the other axes of the coordinate system. It will generally not be orthogonal to the above-defined z-axis and is therefore not suited to be used itself as the axis. Therefore, in step 127, first of all a first cross-product of the largest eigenvector and the z-axis is determined. The direction of the resulting vector is then defined as the direction of the x-axis. To form the direction of the y-axis, in step 128, the cross-product of the defined z-axis from step 125 and the defined x-axis from step 127 is then simply formed.

Alternatively, in step 128, the cross-product of the x-axis that was formed in step 127 and the largest eigenvector that was determined in step 126 can be formed in order to determine a new z-axis. The largest eigenvector is then preserved as the y-axis.

If the method shown in FIG. 12 is used to form a coordinate system, the teeth always appear to be "hanging" regardless of whether they are in fact teeth from the upper jaw or teeth from the lower jaw. Aside from the question of whether the outer maxima or minima are being used in the clearing, this is, however, irrelevant to the functionality of the method.

The method shown in FIG. 13 constitutes a further alternative and advantageous method for deriving an extension line in step 32 (FIG. 3). To do this, in a step 131, first a (possibly simplified) representation that already has a centered and aligned coordinate system is loaded. Possible paths for producing such a coordinate system are shown by the methods in FIGS. 2 and 12. Likewise, in the method from FIG. 13, in a step 132, an extension projection plane is then spanned between the x- and the y-axis. In the following step 133, the entire representation is imaged orthogonally onto the extension projection plane. Then, in step 134, the method of least squares is applied to the thus resulting two-dimensional point cloud, and the curve resulting from it is notated. The curve that has been stipulated in step 134 is then defined in a last step 135 as an extension line.

The advanced embodiment, which was explained for FIGS. 11 and 17 for curves that were approximated as a third-degree polynomial, can likewise be used for the method from FIG. 13, in which starting from the inflection point the inflection tangent is also stipulated as the extension line.

In general, the described technology can be used both after scanning and also during scanning. If the latter should be desired, for example, an image (clone) of the representation can be produced, processed parallel to detection and can be joined together with the representation that is just being detected at a later time. A method that is suitable for this purpose is shown, for example, by the Austrian utility model with application number GM 50210/2016.

FIG. 18 shows a method according to the invention for arriving at an extension line. In a step 181, first a (possibly simplified) representation, which already has a centered and aligned coordinate system, is loaded. Possible ways to produce such a coordinate system or for generating the principal axes of a coordinate system are shown by the methods in FIGS. 2 and 12. One possible way to simplify the representation is shown in FIG. 1.

Then, in a step 182, so-called features within the representation are determined. Features are characteristics that stand out in the surface topography of the representation. They can be, for example, edges and in particular peaks, corners or even depressions of the model. Features are generally determined by identifying extreme changes in the surface curvature. To do this, all points of the model and their spatial relationship to adjacent points are examined individually. If all direct neighbors of a point lie essentially in one plane, the point also lies in one plane. If all neighbors of a point lie essentially in two planes, the point lies on an edge. If the neighbors of a point lie in three or more planes, the point lies on a peak or depression. The manner in which the features are determined is irrelevant to the invention. By way of example, but not limiting, the following methods known from the state of the art are mentioned at this point: "Harris Feature Detector", CenSurE ("Centre Surround Extremas"), ISS ("Intrinsic Shape Signatures"), NARF ("Normal Aligned Radial Feature"), SIFT ("Scale Invariant Feature Transform"), SUSAN ("Smallest Univalue Segment Assimilating Nucleus"), and AGAST ("Adaptive and Generic Accelerated Segment Test").

If the represented objects are teeth, the features can be, for example, protuberances, tips and/or fissures. Aside from teeth with an unusual malposition, it can usually be assumed that these features follow essentially the mandibular arch. They can therefore be used especially advantageously for construction of an extension line.

Analogously to the method that is shown in FIG. 11, in a step 183, an extension projection plane is then spanned between the x- and the y-axis. Of course, this can also take place even before the determination of the features in step 182. One skilled in the art can freely select the sequence of steps 182 and 183 without adversely affecting the function of the method.

In step 184, the determined features of the representation are projected orthogonally, viz. along the z-axis, into the extension projection plane. As also already described for FIG. 11, a two-dimensional point cloud is also formed in this method. However, the two-dimensional point cloud in this case has far fewer elements; this greatly simplifies further computations based on this point cloud and can render the intermediate steps in which strips and centers of gravity of the strips are produced superfluous. Furthermore, with this special two-dimensional point cloud, an especially precise basis for further computations is made available, since features in dental applications can occur only very improbably in regions of the representation that are not part of the teeth (or objects that are modeled after teeth an are located accordingly likewise along the mandibular arch).

The two-dimensional point cloud that was generated in step 184 can then be used as a basis for an extension line. In step 185, the latter can be produced, for example, by the application of the Least Squares Method to the points. As already explained for FIG. 11 and as illustrated in FIG. 17, an especially good approximation to a mandibular arch can be achieved especially well by a third-degree polynomial that follows an inflection tangent starting from its inflection point.

LABELING OF THE FIGURES

FIG. 1
11 Breaking down the model into bricks
12 Voxels in bricks contain surface information?
13 Determining a common location vector for all voxels of the brick
14 Marking of the brick as "empty"
15 Joining all location vectors and empty bricks together into a simplified point cloud FIG. 2
21 Determining of the covariance matrix of the point cloud from steps 11 to 15 (FIG. 1) or step 31 (FIG. 3)
22 Determining of the three eigenvectors of the covariance matrix from step 21
23 Defining of the smallest eigenvector as the direction of the z-axis
24 Defining of the largest eigenvector as the direction of the y-axis
25 Defining of the middle eigenvector as the direction of the x-axis
26 Determining of the center of gravity of the point cloud
27 Defining the center of gravity as the origin of a coordinate system with the axes from steps 23, 24 and 25

FIG. 3
31 (optional) Simplifying the model (see steps 11 to 15 from FIG. 1)
32 Determining of an extension line (for example, the y-axis of the principal major axes, see steps 21 to 27 from FIG. 2 or steps 121 to 128 from FIG. 12; or a curved extension line, see steps 111 to 119 from FIG. 11 or steps 131 to 135 from FIG. 13)
33 Generating of planes of intersection perpendicular to the extension line
34 Projecting onto the planes
35 Determining of the two-dimensional curve (see steps 41 to 43 from FIG. 4)
36 Determining of a center of the curve from step 35
37 Determining of the minima and maxima to the left and right of the center
38 Marking the points of the curve outside of the outer minima or maxima from step 37
39 Removing the points in space or voxels belonging to the marked points of the curve (in step 38)

FIG. 4
41 Determining of the projected points (see steps 51 to 53 from FIG. 5)
42 (optional) Adding of other points by interpolation between two adjacent points at a time
43 (optional) Smoothing (see steps 61 to 63 from FIG. 6)

FIG. 5
51 Defining of strips
52 Determining the centers of gravity of the strips
53 Entering of the centers of gravity as points of the curve FIG. 6
61 Executing of a Fourier transform onto the points from step 41
62 Removing of the high frequencies (all set to zero except the base frequency and first harmonic frequency)
63 Executing of an inverse Fourier transform FIG. 7
71 A smoothed curve (see also steps 61 to 63 from FIG. 6)
72 An unsmoothed curve (see also steps 51 to 53 from FIG. 5)
73 A middle of the curve
74 A first maximum of the curve (left)
75 A second maximum of the curve (right)
76 A region around the middle FIG. 9
91 A symbolic curved extension line FIG. 11
111 Loading of the representation with a coordinate system (see FIG. 2 or FIG. 12)
112 Spanning of an extension projection plane that is spanned from the x- and y-axis of the coordinate system
113 (optional) Defining an extension projection region
114 Projecting of the points of the extension projection region onto the extension projection plane and generating of a 2D point cloud
115 Breaking down the 2D point cloud from step 114 into strips
116 Determining the respective largest and smallest x-values per strip from step 115
117 Forming the arithmetic mean of the two values from step 116 for each strip from step 115
118 Generating of one point per strip from step 115 with the arithmetic mean from step 117 and the center of the strip on the y-axis
119 Creating a curve that is defined as an extension line from the points of step 118

FIG. 12
121 Making available a vector representation, for example from the method from FIG. 1
122 Projecting the vectors of the representation from step 121 onto a unit sphere (Gaussian imaging)
123 Checking of the sphere for a larger free region (without projected vectors)
124 Determining of a center point of the region from step 123
125 Defining the direction of the z-axis of the coordinate system as the direction of the connection from the center point of the unit sphere to the center point of the region from step 124
126 Determining the largest eigenvector of the representation
127 Forming a first cross-product of the z-axis from step 125 and the largest eigenvector from step 127 and defining the first cross-product as the x-axis
128 Forming of a second cross-product from the z-axis and x-axis and defining the second cross-product as the y-axis FIG. 13
131 Loading of the representation with a coordinate system (see FIG. 2 or FIG. 12)
132 Spanning of an extension projection plane between the x- and y-axis of the coordinate system
133 Orthogonal mapping of all points of the (if applicable simplified) representation on the extension projection plane
134 Applying the method of least squares to the mapping from step 133 and noting of the resulting curve
135 Defining of the curve from step 134 as an extension line FIG. 17
171 Extension line approximated as a third-degree polynomial
172 Alternative course of the extension line starting from the inflection point according to the inflection tangent of the polynomial 171

FIG. 18
181 Loading the (if applicable simplified) representation
182 Determining of features
183 Generating an extension projection plane
184 Forming a two-dimensional point cloud by projecting the features from step 182 orthogonally onto the extension projection plane from step 183
185 Forming of a graph along the two-dimensional point cloud from step 184

The invention claimed is:
1. Method for clearing, in particular for removing, unwanted data from optically detected virtual representations of objects, in particular teeth and intraoral structures, the method comprising:

a. Defining an extension line of the representation,
b. Generating a projection plane at one point of the extension line, the extension line at this point being perpendicular to the generated projection plane,
c. Projecting all known points in space of the representation from one region corresponding to the projection plane onto the projection plane, the corresponding point in space being stored for each projected point,
d. Generating a two-dimensional curve on the projection plane from the projected points,
e. Determining maxima, minima and a center of the curve,
f. Identifying projected points of the curve that—viewed from the center of the curve—lie outside of the minima or maxima,
g. Removing the points in space that correspond to the projected points that were identified in f.,
h. Optionally, repeating starting from b. for one further point of the extension line.

2. Method according to claim 1, wherein between a. and b.,
   a1. Subdividing of the extension line into points for the generation of projection planes takes place.

3. Method according to claim 2, wherein two neighboring projection planes border one region of the representation.

4. Method according to claim 3, wherein the region in c. is formed by at least one segment that borders the projection plane.

5. Method according to claim 4, wherein the points in space of each segment are projected at least once.

6. Method according to claim 2, wherein h. takes place until b. to g. have taken place for all points for generating projection planes obtained in a1.

7. The method of claim 2, wherein in a1, the points are distributed equidistantly.

8. Method according to claim 2, wherein the projection in c. takes place along perpendiculars of the projection plane.

9. Method according to claim 3, wherein the projection in c. takes place along perpendiculars of the projection plane.

10. Method according to claim 1, wherein the projection in c. takes place along perpendiculars of the projection plane.

11. Method according to claim 1, wherein the curve in d. is generated by linear interpolation of the projected points on the projection plane.

12. The method according to of claim 11, wherein the curve in d. is generated by equidistant linear interpolation of the projected points on the projection plane.

13. Method according to claim 1, wherein the curve is smoothed.

14. The method according to claim 13, wherein the curve is smoothed by repeated and/or inverse execution of a Fourier transform.

15. Method according to claim 1, wherein the definition of the extension line in a. contains the following:
   a.i. Determining features in the representation,
   a.ii. Generating a two-dimensional point cloud by projection of points, on which features are located, onto an extension projection plane,
   a.ii. Forming of a graph that runs along the point cloud generated in a.ii.,
   a.iv. Defining the graph generated in a.iii. as an extension line.

16. Method according to claim 1, wherein the definition of the extension line in a. contains the following:
   i. Determining the eigenvectors of the representation,
   ii. Defining the longest eigenvector as the direction of the extension line,
   iii. Defining the length of the representation along the longest eigenvector as the length of the extension line.

17. Method according to claim 1, wherein the virtual representation is a TSDF.

18. Method according to claim 1, wherein the represented objects are teeth and that the representation depicts at least two succeeding teeth.

19. The method of claim 18, wherein the representation depicts at least three succeeding teeth.

20. Method according to claim 1, wherein the extension line is a sequence of interconnected straight lines.

* * * * *